(12) United States Patent
Junger

(10) Patent No.: US 7,188,537 B2
(45) Date of Patent: Mar. 13, 2007

(54) BUNG FOR AN ASPIRATION ASSEMBLY

(75) Inventor: Michael Carl Junger, Queensland (AU)

(73) Assignees: William A. Cook Australia Pty. Ltd., Queensland (AU); Cook Urological Incorporated, Spencer, IN (US)

( * ) Notice: Subject to any disclaimer, the term of this patent is extended or adjusted under 35 U.S.C. 154(b) by 230 days.

(21) Appl. No.: 10/993,710

(22) Filed: Nov. 19, 2004

(65) Prior Publication Data

US 2005/0120810 A1 Jun. 9, 2005

Related U.S. Application Data

(60) Provisional application No. 60/523,419, filed on Nov. 19, 2003.

(51) Int. Cl.
*G01N 1/00* (2006.01)
(52) U.S. Cl. .................. 73/864.22; 73/864.74
(58) Field of Classification Search ............. 73/864.22, 73/864.34, 864.73, 864.74; 220/200, 780, 220/789–791, 801–804, 361, 796; 215/355, 215/358, 320, 247; 16/2.3; 604/902, 319, 604/414, 541, 543, 35, 36, 93.01, 415
See application file for complete search history.

(56) References Cited

U.S. PATENT DOCUMENTS

| | | | | |
|---|---|---|---|---|
| 5,029,485 A | * | 7/1991 | Marr ....................... | 73/864.34 |
| 5,232,109 A | * | 8/1993 | Tirrell et al. ............... | 215/247 |
| 5,270,219 A | * | 12/1993 | DeCastro et al. .......... | 436/180 |
| 5,683,658 A | * | 11/1997 | Reischl et al. .............. | 422/102 |
| 5,782,505 A | * | 7/1998 | Brooks et al. ......... | 285/148.19 |
| 5,998,219 A | * | 12/1999 | Costanzo et al. .......... | 436/180 |
| 6,324,926 B1 | * | 12/2001 | Lehtinen et al. ......... | 73/864.24 |

\* cited by examiner

*Primary Examiner*—Robert Raevis
(74) *Attorney, Agent, or Firm*—James B. Hunt

(57) ABSTRACT

A bung for an aspiration assembly sample collection tube, the bung (1) has a top surface (3), a tapered side surface (7) for fitting into the sample tube and a lower surface (5). First and second apertures (9, 11) extend through the bung from the top surface to the bottom surface, the first aperture (9) being for an inlet tubing and the second aperture (11) being for an aspiration tubing, the first aperture has a recess (13) in the lower surface of the bung. This recess is adapted to sealingly receive a supply nozzle of a flushing fluid supply device such as a syringe so that in use flushing fluid may be directed through the inlet tubing.

15 Claims, 3 Drawing Sheets

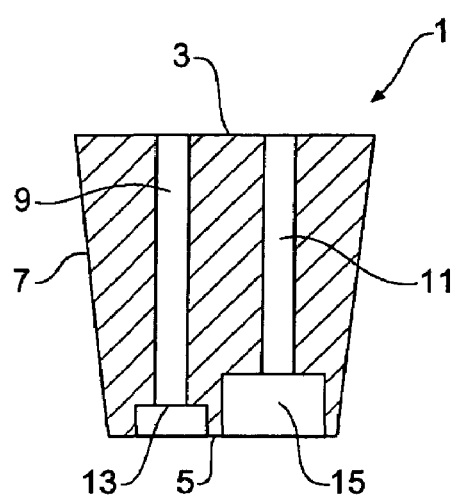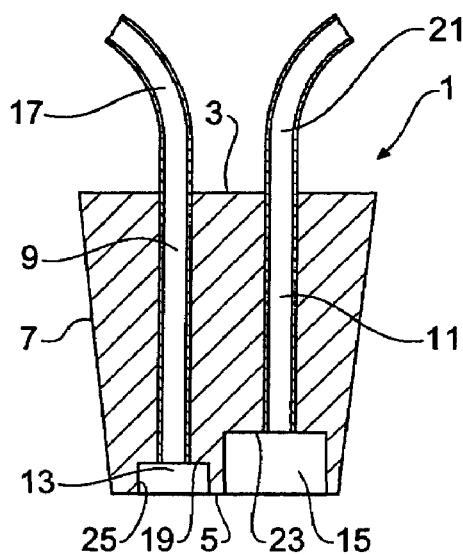
Fig 1    Fig 2
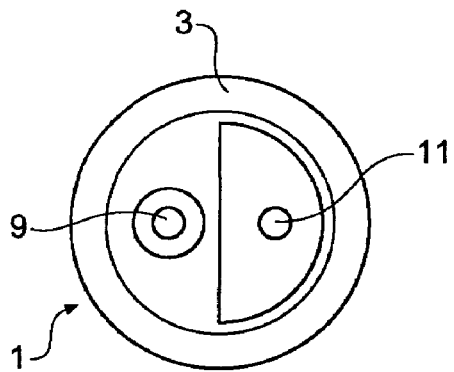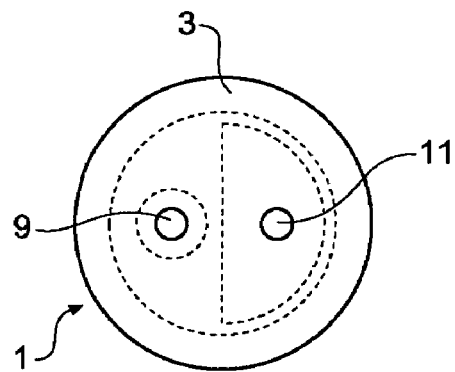
Fig 3    Fig 4
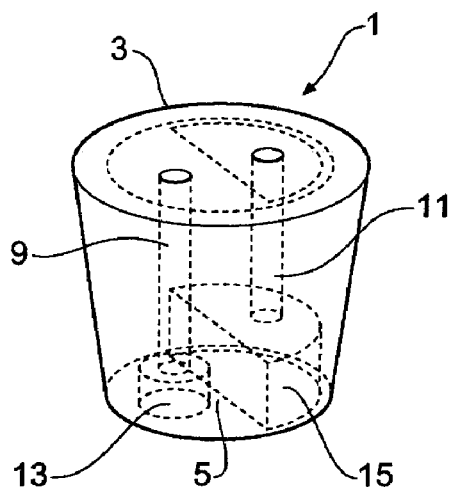
Fig 5

BUNG FOR AN ASPIRATION ASSEMBLY

CROSS-REFERENCE TO RELATED APPLICATIONS

This application claims priority of provisional application Ser. No. 60/523,419, filed Nov. 19, 2003.

TECHNICAL FIELD

This invention relates to a bung for a sample tube and more particularly to a bung for a sample tube used with an aspiration assembly.

BACKGROUND OF THE INVENTION

In an aspiration assembly for extracting an oocyte from a follicle, a needle and tube assembly is used to aspirate an oocyte into a sample tube. The aspiration assembly has a bung which fits into the sample tube and usually there are two apertures through the bung one for the aspirated fluid tubing and the other for tubing connected to a vacuum source.

Before such an aspiration assembly can be used it is important to be able to flush liquid media through the aspiration assembly to check for patency and to remove air from the assembly. One example of a clinical application would be to refill the ovarian follicle and to allow for re-aspiration of the follicular contents. This is done with the aim of using the flow of the pressurised fluid to assist in retrieving the oocyte cumulus complex.

Conventionally flushing and pressurising has been done by placing the tip of a syringe over the inlet tubing and injecting liquid through the inlet tubing to the needle. A problem exists in obtaining a good seal around the inlet tubing and it is towards improving the seal and making the device more convenient to use that the present invention is directed.

Although the invention will be discussed in relation to an application for an aspiration assembly it is to be realised the invention is not so limited but may be used for other applications where similar types of problems exist.

SUMMARY OF THE INVENTION

In one form therefore the invention is said to reside in a bung for an aspiration assembly, the bung having a tapered side surface for fitting into a sample tube, a lower surface, and first and second apertures extending through the bung, the first aperture being for an inlet tubing and the second aperture being for an aspiration tubing, the first aperture including a first recess in the lower surface of the bung, the first recess being adapted to sealingly receive a flushing fluid supply device whereby in use flushing fluid may be directed through the inlet tubing.

In a preferred embodiment of the invention the second aperture also includes a second recess in the lower surface of the bung and preferably the second recess extends further into the bung than the first recess.

In a preferred embodiment the first recess may be dimensioned to sealingly receive the nozzle of a syringe. For this purpose the first recess may be substantially cylindrical in shape.

The first recess may include a sealing surface around the first aperture within the recess. Such a sealing surface may comprise a convex frusto-conical surface tapering away from the first aperture.

In a further form the invention may be said to reside in a bung for an aspiration assembly, the bung having an aperture therethrough and a socket on its lower surface in fluid communication with the aperture to sealingly receive a flushing fluid supply device whereby in use flushing fluid may be directed through the aperture.

In a still further form the invention may be said to reside in an aspiration assembly including a bung, an aspiration needle and a sample collection tubing extending from the aspiration needle to the bung adapted to be engaged into a sample tube, the bung having a tapered side surface for fitting into the sample tube, a lower surface, and first and second apertures extending through the bung to the lower surface, the sample collection tubing extending into the first aperture and the second aperture having an aspiration tubing extending from it to extend to an aspiration device, the first aperture including a recess in the lower surface of the bung, the recess being adapted to sealingly receive a flushing fluid supply device whereby in use flushing fluid can be directed through the sample collection tubing to the aspiration needle.

Preferably the recess has an open end, a base and the sample collection tubing extends through the bung to the base of the recess.

The base of the recess may include a sealing surface around the first aperture. The sealing surface can comprise a convex frusto-conical surface tapering away from the first aperture.

In a further form the invention may be said to reside in a bung for a sample tube, the bung having a first insertion end for insertion into the sample tube and second exterior end and a fluid flow channel extending through the bung between the first end and the second end and wherein the fluid flow channel includes at the insertion end an engagement portion recessed into the bung, the engagement portion being adapted to receive and substantially seal against an outlet of a flushing fluid supply device.

The bung according to the various embodiments may be manufactured from a resilient elastomeric material such as a silicone rubber or a thermoplastic elastomer.

BRIEF DESCRIPTION OF THE DRAWING

This then generally describes the invention but to assist with understanding reference will now be made to the accompanying drawings which show preferred embodiments of the invention.

In the drawings:

FIG. 1 shows a cross-section of a first embodiment of a bung according to the present invention;

FIG. 2 shows the embodiment shown in FIG. 1 with the aspiration and inlet tubes joined into the bung;

FIG. 3 shows an underneath view of the bung as shown in FIG. 1;

FIG. 4 shows a top view of the bung shown in FIG. 1;

FIG. 5 shows a general perspective view of the bung shown in FIG. 1 with the internal components shown dotted;

DETAILED DESCRIPTION

Figure 6A:
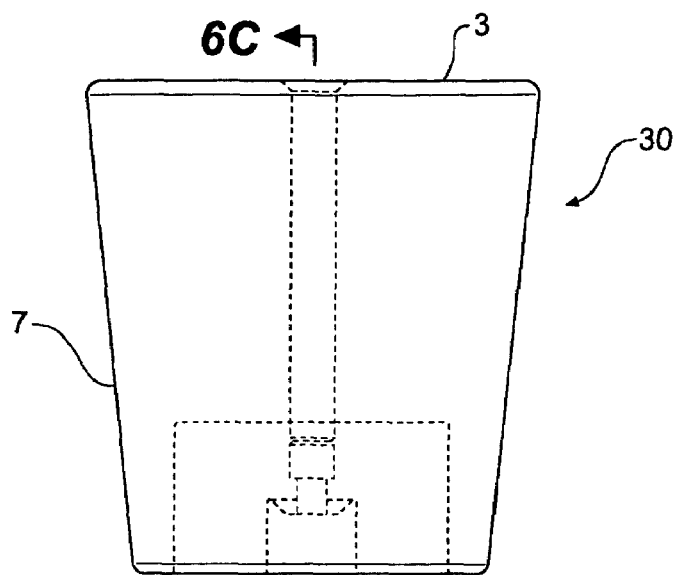
FIGS. 6A, 6B and 6C show various views of a second embodiment of a bung according to the present invention.

Now looking at the first embodiment shown in FIGS. 1 to 5 it will be seen that the bung 1 has an upper surface 3 a lower surface 5 and a tapered side surface 7. Extending through the bung 1 are an inlet aperture 9 and an outlet aperture 11. At the base of the inlet aperture 9 is an inlet recess 13 and at the base of the aspiration aperture 11 is an outlet recess 15. It will be noted that the outlet recess 15 is deeper or extends further into the bung than the inlet recess 13.

As can be particularly seen in FIG. 2 a sample collection tubing 17 extends into the inlet aperture 9 and extends to the base 19 of the recess 13. Similarly an aspiration tubing 21 extends to the base 23 of the outlet recess 15.

When it is desired to flush the sample collection tubing 17, a flushing fluid supply device such as the nozzle of a syringe may be placed into the recess 13 to seal against the base 19 and flushing fluid can be directed through the sample collection tubing 17. Conveniently the dimensions of the recess 13 are such that the sides 25 and base 19 of the recess 13 seal against the sides and tip of the nozzle of a syringe.

Figure 6B:
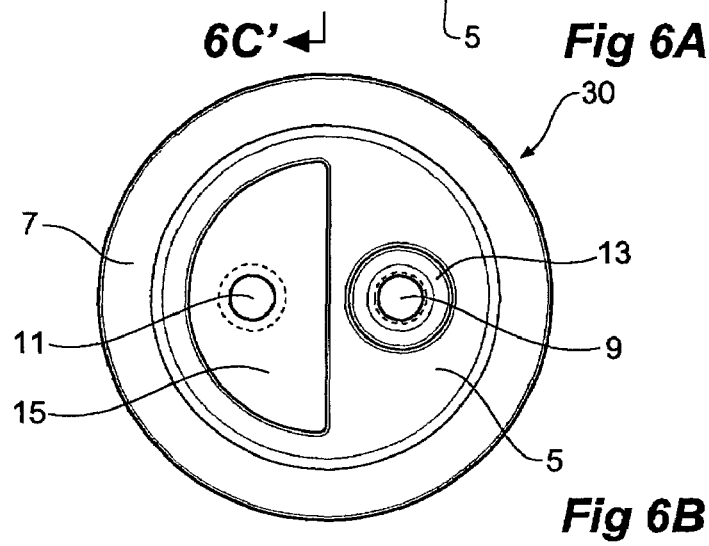
Figure 6C:
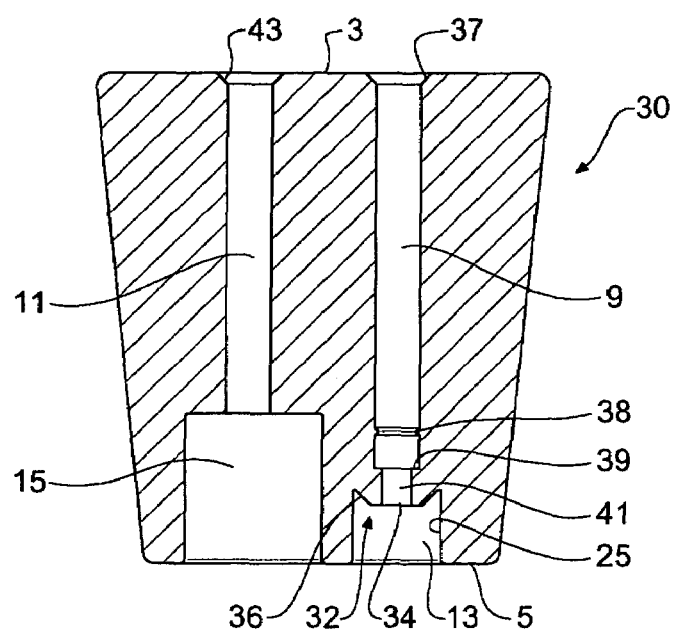

FIGS. 6A, 6B and 6C show a second embodiment of a bung according to the present invention. Those features of the embodiment shown in FIGS. 6A, 6B and 6C that are same as embodiment shown in FIG. 6A shows a side view of a second embodiment of the bung according to the invention. FIG. 6B shows and underneath view of the bung shown in FIG. 6A. FIG. 6C shows a cross section along the line 6C–6C' of FIG. 6A.

The bung 30 has an upper surface 3, a lower surface 5 and a tapered side surface 7. Extending through the bung 30 are an inlet aperture 9 and an outlet aperture 11. At the base of the inlet aperture 9 is an inlet recess 13 and at the base of the aspiration aperture 11 is an outlet recess 15. It will be noted that the outlet recess 15 is deeper or extends further into the bung than the inlet recess 13. The outlet aperture 11 has a chamfer 43 at its entrance on the upper surface 3 of the bung 30 to assist with the placement of an aspiration tubing into the outlet aperture 11. The inlet aperture 9 has a chamfer 37 at its entrance on the upper surface 3 of the bung 30 to assist with the placement of an sample collection tubing into the inlet aperture 9.

The inlet aperture 9 has an integral sealing ring 38 towards its lower end to assist with sealing onto a sample collection tubing when inserted into the inlet aperture. A shoulder 39 at the base of the inlet aperture 9 and a portion of lesser diameter 41 provide support and a stop for the sample collection tubing when it is inserted into the inlet aperture 9.

In this embodiment the base 32 of the recess 13 of the bung 30 has a sealing surface 36 around the aperture 9 to assist with sealing. The sealing surface 36 on the base 32 is a convex frusto-conical surface tapering away from the opening 34 to the aperture 9 to the side surfaces 25 of the recess 13.

The bung is manufactured from a resilient material such as a silicone elastomer or a thermoplastic elastomer and hence the sealing surface 36 provides a good seal on to the tip of the nozzle of a syringe.

Figure 7:
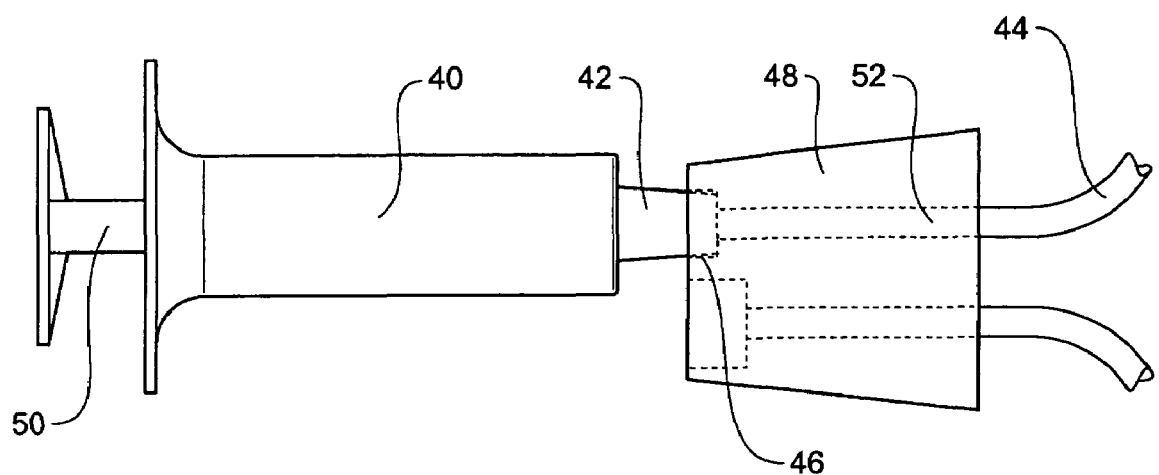
FIG. 7 shows the bung according to the present invention set up for flushing using a syringe.

The use of a syringe is shown in FIG. 7. Syringe 40 has a nozzle 42 which, when it is desired to flush the sample collection tubing 44, is placed into a recess 46 in the bung 48. The plunger 50 of the syringe can be activated to push flushing fluid through the aperture 52 in the bung 48 and the sample collection tubing 44.

Figure 8:
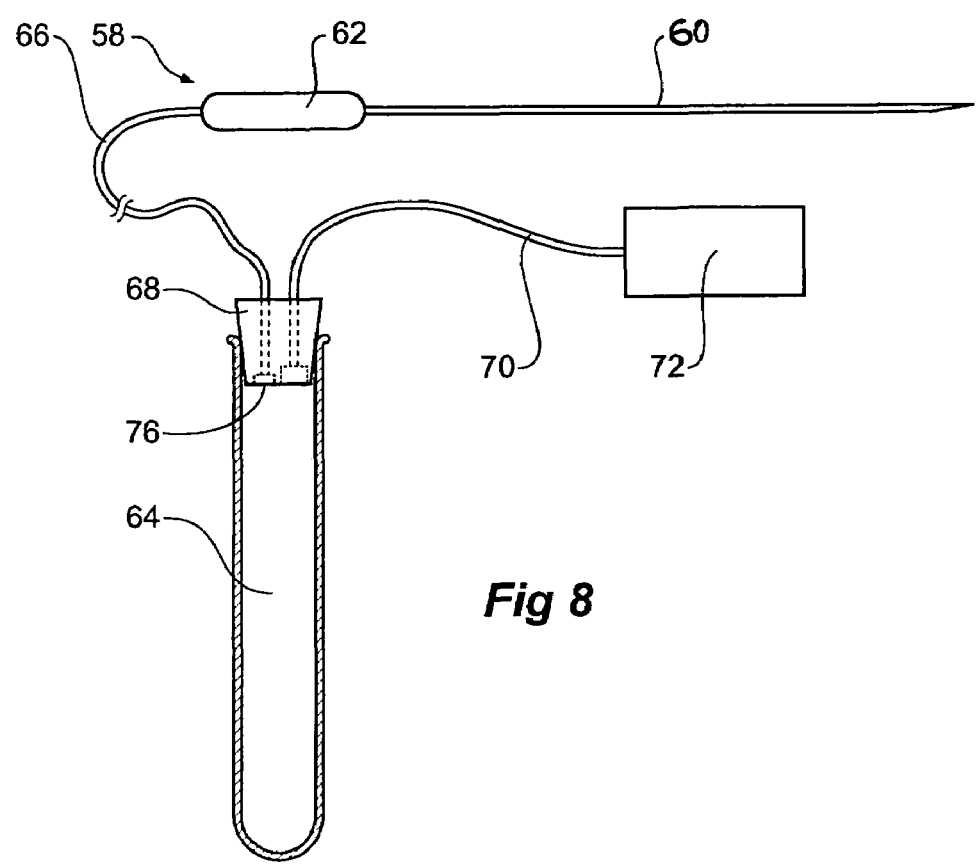
FIG. 8 shows an aspiration assembly according to the present invention.

One embodiment of aspiration catheter which can be used with a bung according to the present invention is shown in FIG. 8. In this embodiment the aspiration device 58 includes an aspiration needle 60 extending from a handle 62. A sample collection tube 64 is connected to the handle 62 and hence the needle 60 by a sample collection tubing 66 and bung 68. The bung fits into the sample collection tube 64.

Also extending through the bung 64 is an aspiration tubing 70 extending to a vacuum source 72.

In the process of collecting an oocyte and ovum the needle 60 is inserted into a human or animal follicle in an ovary and when a follicle is punctured the vacuum source 72 is activated to create a suction through the sample tube 64, sample collection tubing 66 and needle 60 to draw an oocyte into the sample tube 64.

As discussed earlier it is useful to be able to provide flushing fluid through the sample collection tubing 66, handle 62 and needle 60 to ensure no air is in the aspiration system before it is used and for this purpose before the bung 68 is placed into the sample collection tube 64 flushing fluid can be directed through the bung into the sample collection tubing 66 by placing the nozzle of a syringe into the recess 76 of the bung 68 before the bung 68 is placed into the sample collection tube 64.

Throughout this specification various indications have been given as to the scope of the invention but the invention is not limited to any one of these but may reside in two or more of these combined together.

What is claimed is:

1. A bung for an aspiration assembly, the bung having a tapered side surface for fitting into a sample tube and a lower surface, first and second apertures extending through the bung, the first aperture being for an inlet tube and the second aperture being for an aspiration tube, the first aperture including a first recess in the lower surface of the bung, the first recess being adapted to sealingly receive a flushing fluid supply device whereby in use flushing fluid may be directed through the inlet tube, the second aperture also including a second recess in the lower surface of the bung and the second recess extending further into the bung than the first recess.

2. A bung for an aspiration assembly as in claim 1 wherein the first recess is dimensioned to sealingly receive the nozzle of a syringe.

3. A bung for an aspiration assembly as in claim 1 wherein the first recess is substantially cylindrical in shape.

4. A bung for an aspiration assembly as in claim 1 wherein the first recess includes a sealing surface around the first aperture within the recess.

5. A bung for an aspiration assembly as in claim 3 wherein the sealing surface comprises a convex frusto-conical surface tapering away from the first aperture.

6. A bung for an aspiration assembly as in claim 1 wherein the bung is manufactured from a resilient elastomeric material.

7. A bung for an aspiration assembly as in claim 6 wherein the resilient elastomeric material is selected from the group comprising silicone rubber and thermoplastic elastomer.

8. A bung for an aspiration assembly as in claim further including an aspiration assembly and wherein the aspiration assembly includes an aspiration needle and a sample collection tubing extending from the aspiration needle to the bung, the sample collection tubing extending into the first aperture and the second aperture having an aspiration tubing extending from it to extend to an aspiration device.

9. A bung for an aspiration assembly as in claim 8 wherein the recess has an open end and a base and the sample collection tubing extends through the bung to the base of the recess.

10. A bung for an aspiration assembly as in claim 9 wherein the base of the recess includes a sealing surface around the first aperture.

11. A bung for an aspiration assembly as in claim 10 wherein the sealing surface comprises a convex frusto-conical surface tapering away from the first aperture.

12. An aspiration assembly including a bung, an aspiration needle and a sample collection tubing extending from the aspiration needle to the bung adapted to be engaged into a sample tube, the bung having a tapered side surface for fining into the sample tube and a lower surface, first and second apertures extending through the bung to the lower surface, the sample collection tubing extending into the first aperture and the second aperture having an aspiration tubing extending from it to extend to an aspiration device, the first aperture including a recess in the lower surface of the bung, the recess being adapted to sealingly receive a flushing fluid supply device whereby in use flushing fluid can be directed through the sample collection tubing to the aspiration needle.

13. An aspiration assembly as in claim 12 wherein the recess has an open end and a base and the sample collection tubing extends through the bung to the base of the recess.

14. An aspiration assembly as in claim 13 wherein the base of the recess includes a sealing surface around the first aperture.

15. An aspiration assembly as in claim 14 wherein the sealing surface comprises a convex frusto-conical surface tapering away from the first aperture.

* * * * *